United States Patent [19]

Kondo et al.

[11] 4,256,693

[45] Mar. 17, 1981

[54] MULTILAYERED INTEGRAL CHEMICAL ANALYSIS ELEMENT FOR THE BLOOD

[75] Inventors: Asaji Kondo; Masao Kitajima, both of Asaka, Japan

[73] Assignee: Fuji Photo Film Co., Ltd., Minami-ashigara, Japan

[21] Appl. No.: 46,125

[22] Filed: Jun. 6, 1979

[30] Foreign Application Priority Data

Jun. 6, 1978 [JP] Japan .................. 53-77177[U]

[51] Int. Cl.³ .............. G01N 33/48; G01N 33/06; G01N 33/52
[52] U.S. Cl. .......................... 422/56; 422/57; 435/805
[58] Field of Search .............. 422/56, 57; 435/805

[56] References Cited

U.S. PATENT DOCUMENTS

| 3,554,871 | 1/1971 | Lariccia | 435/805 X |
|---|---|---|---|
| 3,663,374 | 5/1972 | Moyer . | |
| 4,042,335 | 8/1977 | Clement | 422/56 |
| 4,050,898 | 9/1977 | Goffe | 422/57 |
| 4,061,468 | 12/1977 | Lange | 422/56 |
| 4,144,306 | 3/1979 | Figueras | 422/56 |
| 4,160,008 | 7/1979 | Fenocketti | 422/56 |
| 4,166,093 | 8/1979 | Smith-Lewis | 422/56 |

*Primary Examiner*—Sidney Marantz
*Attorney, Agent, or Firm*—Sughrue, Rothwell, Mion, Zinn and Macpeak

[57] ABSTRACT

A multilayered integral chemical analysis element for the blood comprising a filter layer capable of removing formed components from the blood, a water-proof layer having at least one small opening therein, a porous spreading layer and a reagent layer laminated in this order.

5 Claims, 1 Drawing Figure

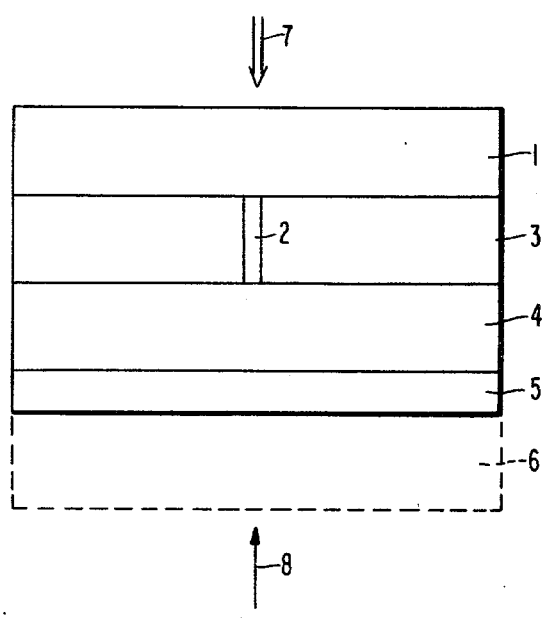

MULTILAYERED INTEGRAL CHEMICAL ANALYSIS ELEMENT FOR THE BLOOD

BACKGROUND OF THE INVENTION

1. Field of the Invention

This invention relates to a multilayered integral chemical analysis element for the blood, and, in particular, to an element which permits the assay of whole blood.

2. Description of the Prior Art

Blood samples for use in analyzing chemical components of the blood, e.g., glucose, albumin, calcium, urea, uric acid, bilirubin, glycerol, cholesterol, cho lesterol ester, etc., include whole blood and the fluid part of blood left after performing a troublesome operation of removing the formed components, i.e., the plasma or serum. Needless to say, the use of whole blood permits simple and rapid determination of the chemical components of blood and is especially desirable for analyzing the blood in the case of an emergency.

Due to technical difficulties, a dry-method of chemically analyzing blood simply and rapidly using whole blood as a sample and an analytical material therefor have not yet been provided. For a simple and rapid dry assay of blood, inventions in which a multilayered integral chemical analysis element comprising a water-impermeable and light-permeable (transparent) support, a reagent layer and a porous spreading layer laminated in this order, and a multilayered integral chemical analysis element of the same structure as above except that a filter layer is formed on the porous spreading layer have been described, for example, Japanese Patent Applications (OPI) Nos. 11395/74 (U.S. Pat. No. 3,663,374), 53888/74 (U.S. Pat. No. 3,992,158), 137192/75 (U.S. Pat. No. 3,983,005), 40191/76 (U.S. Pat. No. 4,042,335), 3488/77 (U.S. Pat. No. 4,066,403), 131786/77 (U.S. Pat. No. 4,050,898), 142584/77 (U.S. Pat. No. 4,053,381) and 24893/78 (U.S. patent application Ser. No. 715,796, filed Aug. 19, 1976), abandoned, and U.S. Pat. Nos. 3,992,158 and 3,526,480. (The term "OPI" as used herein refers to a "published unexamined Japanese patent application".) These analysis elements are used in an assay in which the blood serum is used as an assay sample. The procedure itself is simple, but the serum must be separated from the whole blood and this is a troublesome operation which cannot be omitted. Thus, these conventional elements, and assays do not meet emergency needs.

Japanese Patent Application (OPI) No. 11395/74 (U.S. Pat. No. 3,663,374) discloses a method of determining the oxygen in the blood using whole blood as a sample by removing formed components using a sheet-like filter. Such a method, however, is not suited for general application, because the material, device and the method of operation used are special.

The term "formed components" as used herein means leucocytes (granulocyte, lymphocyte and monocyte), earthrocytes and platelets.

SUMMARY OF THE INVENTION

It is an object of this invention to provide a blood analysis element which can determine the chemical components of the blood rapidly and easily by a dry-method using whole blood as an assay sample.

According to this invention, there is provided a multilayered integral chemical analysis element for the blood, comprising a filter layer capable of removing formed components in the blood, a water-proof layer having at least one small opening therein, a porous spreading layer, and a reagent layer laminated in this order.

In another aspect, this invention also provides a multilayered integral chemical analysis element for the blood which has the above structure and further includes a support capable of maintaining the laminated state of the four layers.

BRIEF DESCRIPTION OF THE ACCOMPANYING DRAWING

The FIGURE is a schematic cross-section of the multilayered integral chemical analysis element for the blood in accordance with this invention, which also shows the position and direction of application of the sample and the direction from which the result of the chemical analysis is observed.

DETAILED DESCRIPTION OF THE INVENTION

The structure and an example of use of the multilayered integral chemical analysis element for the blood of this invention are described in detail below with reference to the FIGURE.

Referring to the FIGURE, the reference numeral 1 represents a filter layer for removing formed components of blood. This layer is present over the entire surface of a water-proof layer 3 having a small opening 2 therein, or may be present in a defined area on the top surface of layer 1 at the periphery to thereby define a small opening 2, for example, in a circular area having a radius from the center of the opening of about 5 mm to about 1 cm. The water-proof layer 3 is provided in contact with the filter layer. Except for the opening, the water-proof layer must be substantially water-impermeable. It may be permeable or impermeable to light, or be light-reflecting.

Beneath the water-proof layer 3 is provided a porous spreading layer 4. The purpose of this layer is to receive the fluid sample which has flown through the opening in the water-proof layer 3, and to spread it uniformly in the horizontal and perpendicular directions without changing its constituent components, thus supplying the fluid sample uniformly to a reagent layer 5 beneath the spreading layer 4. The reagent layer 5 contains various reagents for analyzing certain components of blood by utilizing the reagent's ability to form color or discolor upon contact with the reagent in the layer. This layer may consist of one or more constituent layers.

The four layers described above may be formed on a transparent support 6.

In analyzing blood using the multilayered integral chemical analysis element of this invention, a suitable amount (about 5 $\mu l$ to several hundred $\mu l$) of blood is dropped at position 7 onto that portion of the filter layer which is immediately above the opening 2. The formed components of the whole blood are filtered out by the filter layer, and only the fluid portion reaches the surface of the water-proof layer 3. A portion of this fluid is supplied to the porous spreading layer 4 in an amount controlled by passage through the opening 2, and is spread into an area about 10 mm in diameter by the porous spreading layer 4. The fluid thus reaches the reagent layer 5 where a coloration reaction or a discoloration reaction takes place. The degree of coloration or discoloration is evaluated by the eye or by a photometer from the direction 8.

In the unit of this invention, an area as small as several square centimeters is sufficient for one analysis. As will be appreciated from the foregoing description, analysis of blood with the element of this invention requires only the dropping a certain amount of whole blood onto the analysis element, and does not require removal of formed components nor handling of liquid reagents prior to assay. Thus, it permits simple and rapid chemical analysis by a dry-method using whole blood as an assay sample, and can fully meet emergency needs.

The term "chemical analysis", as used in this application, means the identification and/or determination (quantification) of components of a sample fluid by spectral analysis such as light absorption analysis, light reflecting analysis and colorimetric analysis.

A characteristic feature of the present invention is that the filter layer and the porous spreading layer are laminated and bonded through the interventing water-proof layer having a small opening therein. It is known from the disclosures of the above-cited patent specifications that (1) the formed components of blood can be removed by sheet filtration, and (2) a multilayered chemical analysis sheet equipped with a porous spreading layer can permit dry-chemical analysis of the blood plasma or serum left after removal of formed components. A combination of findings (1) and (2) does not ensure uniform arrival and supply of the fluid part of whole blood left after removal of formed components at the porous spreading layer, and therefore, it is difficult to utilize the characteristic of the conventional multilayered integral chemical analysis sheet in arriving at the present invention.

On extensive investigations, it has been found that by interposing a water-proof layer having a small opening between the filter layer and the porous spreading layer of a conventional multilayered chemical analysis sheet, the fluid part of blood left after removal of formed components by the filter layer is pooled and held on the water-proof layer, and subsequently, only a controlled amount of the fluid is supplied to the porous spreading layer through the opening. Accordingly, with the present invention a fixed amount of plasma or serum is supplied to the reagent layer simply and without the care which is required to supply the assay sample to conventional analysis elements.

The materials and constructions of the individual layers of the multilayered analysis element of this invention are described in greater detail below.

The filter layer serves to separate the formed components of the blood, and pass only the fluid part to the underlying layers. The filter layer may be made of, for example, one or more of paper (e.g., filter paper, tissue paper, etc.), non-woven fabric, sheet-like filter material composed of powders or fibers such as man-made fibers or glass fibers, and membrane filter having suitable pore sizes. The filter layer separates the formed components of the blood at one time, or successively, for example in the order of leucocytes, erythrocytes, and platelets.

The thickness of the filter layer is from about 8 $\mu$m to about 1 mm (depending upon the filter, from several tens of $\mu$m to several mm), preferably from about 100 $\mu$m to about 1 mm. To prevent hemolysis of the whole blood on contact with the filter layer, the material of the filter layer may be treated with chemicals, such as those disclosed in U.S. Pat. No. 3,552,928. For instance, water-soluble amino acids are effective in causing separation of the colored red cells from the whole blood. Specific examples of the filter layer are a layer composed of a laminate of a membrane filter having a pore diameter of 8 $\mu$m and a membrane filter having a pore diameter of 1.2 $\mu$m both having a thickness of 100 $\mu$m, a layer composed of a laminate of a filter paper and a membrane filter, and a layer composed of a laminate of tissue paper and a membrane filter. Suitable examples of the material for the filter layer include Schleicher and Schuell Filter Paper Nos. 2316 and 507, Whatman GF/A Glass Fiber Paper, etc.

The water-proof layer is in the form of a plate or film. It is made of a metal such as an aluminum foil, cellophane-film, paper such as paraffin paper, polymer laminate papers and water-proof papers, or a synthetic resin such as polyethylene, polypropylene, polyvinyl chloride, saran (a vinylidene chloride/vinylchloride copolymer), polycarbonate, polyesters (e.g., polyethylene terephthalate), and cellulose esters (e.g., cellulose triacetate). Those materials which are impermeable to water can be used. If desired, the surface of such a material may be subjected to a water-repelling treatment in a customary manner using an organopolysiloxane or a perfluoroalkylated compound. The thickness of the water-proof layer is about 5 $\mu$m to about 1 mm, preferably from about 15 $\mu$m to about 0.5 mm.

The small opening provided in the water-proof layer may be triangular or circular, and range in size from a pinhole (about 30 $\mu$m in diameter) to about 5 mm in diameter. The number of openings is normally one per spot of sample, but a plurality of holes of small diameters (with a diameter of about 30 $\mu$m to about 0.5 mm) may be provided in numbers of two or more. When two or more holes are provided, it is preferable to arrange these holes within a circle having a diameter of about 1 mm to about 5 mm. If desired, these small holes may be mere cuts in the form of *, + or —. When the water-proof layer is made of a white material containing a white dye or pigment or a reflecting material such as aluminum foil, it is a good background for observing discoloration or coloration at the time of measurement.

To fix the water-proof layer on the porous spreading layer, a solution of a water-proofing material which will form the water-proof layer may be coated on the spreading layer. However, it is preferable to fix a separately produced water-proof layer to the developing layer using an adhesive. Pressure-sensitive, thermosensitive, solvent-based, and reactive adhesives may be used as the adhesive for this purpose. The pressure-sensitive adhesives are preferred because the manufacturing operation for the analysis element is simple. When fixing the water-proof layer to the spreading layer the adhesive should not penetrate deep into the spreading layer, and should not be damaged by water. As the water-proof layer having a small opening marketed pressure-sensitive adhesive tapes or sheets of polyethylene terephthalate, polyvinyl chloride, cellophane film or an aluminum foil may be used after providing an opening therein. Such adhesive tapes or sheets are easily fixed on the spreading layer.

In addition to the filter layer and the water-proof layer, a porous spreading layer, a reagent layer and a support can be used in the multilayered integral chemical analysis element of this invention, as described in detail in the above-cited patent specifications.

The porous spreading layer may be a porous non-fibrous membrane typified by a membrane filter, a porous film of particulate matter typified by a polymer containing fine particles, or a fibrous membrane, which has a small chromatographic effect, as disclosed in U.S. Pat. No. 3,992,158.

The reagent layer comprises reagents which form colors or discolor upon the direct or indirect reaction with the components of an assay sample which are included in a hydrophilic binder (such as gelatin or polyvinyl alcohol) as disclosed in U.S. Pat. No. 3,983,005, or a hydrophobic binder as disclosed in U.S. Pat. No. 4,066,403.

The support is made of a material having good transparency such as polyesters, polycarbonate, or cellulose esters which may be a film having a thickness in the range of about 10 $\mu$m to about 0.5 mm. If a semi-transparent or non-transparent paper or transparent or non-transparent tape coated with a mold releasing agent such as silicones is bonded to the reagent layer, it serves as a protecting cover, and the measurement can be conducted after peeling off such a paper or tape.

Conventional multilayered integral chemical analysis elements are in sheet form, but the element of this invention may also be a plate or rod when it is fixed on the appropriate support. Accordingly, the multilayered integral chemical analysis element of this invention also embraces the conventional multilayered integral chemical analysis sheets such as those disclosed in U.S. Pat. No. 3,992,158. Preferably, the element of this invention is in the form of a sheet or thin tape.

In additon to using an adhesive in laminating the individual layers of the element of this invention, the adhesive ability of the binders used in the individual layers may be utilized. For example, the reagent layer is laminated by coating a reagent solution containing gelatin as a binder on the support and drying the coating. Then, as the porous spreading layer, a membrane filter wetted with water and partially dried is superimposed on the reagent layer to bond these layers spontaneously. Further, the water-proof layer and the filter layer may be laminated using a pressure sensitive adhesive to form a unitary structure. This procedure easily permits mass-production.

In describing the present invention, the description has been directed to an embodiment in which whole blood is used as an assay sample. Likewise, lymphatic fluid, urine, and other body fluids containing organic components (solid components) can be analyzed with the element of this invention. The fluid of use of the multilayered integral chemical analysis element of this invention is not limited to the quantitative or qualitative analysis of blood as one skilled in the art would readily realize.

The multilayered integral chemical analysis element for the blood in accordance with this invention has the following features and advantages.

(1) Since whole blood can be directly used as an assay sample, the processing operation is very simple and convenient. Furthermore, the preparation time up to chemical analysis itself is very short. Despite this, the element of this invention can permit dry-chemical analysis of blood with accuracy equivalent to wet-method chemical analysis of components dissolved in blood using the serum or plasma as an assay sample.

(2) The sample fluid resulting from the filtration of formed components from the whole blood dropped onto the filter layer is supplied smoothly to the spreading layer through the opening provided in the water-proof layer. Furthermore, in the spreading layer, the sample fluid is spread sideways very smoothly. Thus, the time required for spreading is not longer than in the conventional analysis elements which do not have a filter layer and a water-proof layer. In other words, the filter layer and the water-proof layer do not impede the admission and spreading of the sample fluid.

(3) According to a conventional method, a liquid droplet at the forward end of a pipette must be carefully contacted with the porous spreading layer in spotting the sample fluid. If the liquid droplet is spotted in a disorderly manner, the liquid may flow on the porous spreading layer, or the spread pattern may become irregular, thus hampering the determination. In contrast, with the element of this invention, no attention needs to be paid to the spotting of a sample fluid (whole blood). Whether the sample blood is supplied by spotting it in a disorderly manner from a pipette, or by including the sample in a small ball of absorbent cotton and causing it to be stroked on the opening in the filter layer, the sample is supplied to the porous spreading layer only through the opening. Thus, the spread pattern of the sample is nearly circular. Hence, the multilayered integral chemical analysis element for the blood of this invention makes the application of the sample very easy.

(4) The sample fluid which has flown for analysis into the analysis element through the opening is prevented from evaporation of water by the water-proof layer. Thus, it maintains the reagent layer in the wet state for 20 to 30 minutes or longer, and holds water in an amount sufficient for performing reaction in an aqueous solution.

(5) The porous spreading layer is intrinsically brittle and weak owing to its porous nature. Since in an analysis sheet of the conventional type, this layer is located at the uppermost position and exposed, its handling requires great care before and during use. However, in the element of this invention, a greater portion of the surface of the weak porous spreading layer is protected by the filter layer and/or the water-proof layer, and therefore, the operability of the analysis element is markedly increased.

(6) When the analysis element of this invention includes a support, the reagent layer is protected from the outer atmosphere by the water-proof layer and the lowermost support. In the conventional element, the uppermost layer is the porous spreading layer, and therefore, one surface of the reagent layer is substantially exposed to the outer atmosphere. The element of this invention has good storage stability because both surfaces of the reagent layer are protected airtight.

(7) When in the element of this invention, a white material containing a white dye or pigment, or an aluminum foil is used as the water-proof layer this layer plays a role of an effective light reflector at the time of optically detecting the colored portion of the reagent layer. Hence, this increases the accuracy of the quantitative analysis.

While the invention has been described in detail and with reference to specific embodiments thereof, it will be apparent to one skilled in the art that various changes and modifications can be made therein without departing from the spirit and scope thereof.

What is claimed is:

1. A multilayered integral chemical analysis element for a blood sample, said element comprising a filter layer capable of removing formed components comprising leucocytes, erythrocytes and platelets in the blood, a water-proof layer having at least one small opening therein, a porous spreading layer, and a reagent layer laminated in this order.

2. The element of claim 1 which further comprises a support for maintaining the laminated state of said four layers.

3. The element of claim 1, wherein said small opening is circular or triangular, or is a cut in the form of *, +, or −.

4. The element of claim 1, wherein the number of said small openings is one per spot of blood sample, and said small opening is circular or triangular and ranges in size from about 30 μm to about 5 mm in diameter.

5. The element of claim 1, wherein two or more small openings ranging in size from about 30 μm to about 0.5 mm in diameter are provided per spot of blood sample, said small openings being circular or triangular and being arranged within a circle having a diameter of about 1 mm to 5 mm.

* * * * *